United States Patent [19]

Ripke

[11] Patent Number: 4,977,253

[45] Date of Patent: Dec. 11, 1990

[54] PROCESS FOR THE SULFATION OF ALKYLOLIGOGLYCOSIDES

[75] Inventor: Norbert Ripke, Haltern, Fed. Rep. of Germany

[73] Assignee: Huels Aktiengesellschaft, Marl, Fed. Rep. of Germany

[21] Appl. No.: 388,499

[22] Filed: Aug. 2, 1989

[30] Foreign Application Priority Data

Oct. 13, 1988 [DE] Fed. Rep. of Germany ....... 3834911

[51] Int. Cl.$^5$ .......................... C07H 1/00; C07G 3/00; C08B 37/00
[52] U.S. Cl. .................................... 536/118; 536/122; 536/124
[58] Field of Search ....................... 536/118, 122, 124; 252/174.17

[56] References Cited

U.S. PATENT DOCUMENTS 4,483,787  11/1984  Jones et al. .................... 252/174.17
4,814,437  3/1989  De Belder et al. ................. 536/118

FOREIGN PATENT DOCUMENTS 8801640  3/1988  World Int. Prop. O. .

Primary Examiner—Ronald W. Griffin
Assistant Examiner—Everett White
Attorney, Agent, or Firm—Oblon, Spivak, McClelland, Maier & Neustadt

[57] ABSTRACT

An alkyloligoglycoside having an alkyl group content of 8 to 22 carbon atoms and having an average degree of oligomerization of 1 to 5 is sulfated with a sulfating agent in an organic solvent having a boiling point of 30° to 100° C.

9 Claims, No Drawings

PROCESS FOR THE SULFATION OF ALKYLOLIGOGLYCOSIDES

BACKGROUND OF THE INVENTION

1. Field of the Invention:

The present invention relates to a process for the sulfation of alkyloligoglycosides.

2. Discussion of the Background:

Sulfated alkyloligoglycosides are useful as foaming agents and dispersants in rinsing agents, detergents, and cleansers. They are anionic surfactants which are used in the formulation of cosmetics and are used in tertiary petroleum recovery.

U.S. Pat. No. 1,951,784 describes sulfuric acid esters of alkyloligoglycosides which are prepared by the simultaneous reaction of saccharides or starch with sulfuric acid and an alcohol. In this process, sulfuric acid esters of the alcohols used are also formed to a substantial extent, which clearly reduces the yield of the desired product. However, if the starting materials are alkyloligoglycosides that have a melting point in the range of 150° C., sulfation temperatures above 100° C. are necessary. At these temperatures, acetal cleavage occurs, whereupon the liberated alcohols are likewise converted to sulfuric acid esters. Glucose is also liberated, which is charred to carbon under these conditions.

EP-A-280 715 describes a process in which alkylglycosides are sulfated using a sulfur trioxidetrimethylamine complex in dimethylformamide under mild conditions in 19 to 24 hours. This process is costly because of the use of the special reagent. The high boiling point is also a drawback in the recovery of solvent by distillation. A need therefore continues to exist for a method of sulfating alkyloligoglycosides under mild conditions.

SUMMARY OF THE INVENTION

Accordingly, one object of the invention is to provide a method of sulfating alkyloligoglycosides under mild reaction conditions.

Briefly, this object and other objects of the present invention as hereinafter will become more readily apparent can be attained in a method of sulfating alkyloligoglycosides whose alkyl groups contain from 8 to 22 carbon atoms and which have an average degree of oligomerization of 1 to 5, with a sulfating agent in an organic solvent having a boiling point of 30° to 100° C.

DETAILED DESCRIPTION OF THE PREFERRED EMBODIMENTS

The important feature of the present invention is that the sulfation is conducted using conventional sulfating agents in an inert organic solvent having a boiling point (under standard conditions) of 30 to 100° C. Such known sulfating agents as chlorosulfonic acid, sulfur trioxide, 70 to 100% sulfuric acid and sulfuric acid containing sulfur trioxide which may contain up to 70 moles of sulfur trioxide per 100 moles of sulfuric acid, may be employed.

Alkyloligoglycosides that contain branched or unbranched alkyl groups of 8 to 22 carbon atoms are used for the sulfation. Preferably used are alkyloligoglycosides having alkyl groups containing 10 to 16 carbon atoms. Alkyloligoglycosides having an average degree of oligomerization of 1 to 5 are normally used. In the context of this invention, alkylglycosides having a degree of oligomerization of one are also alkyloligoglycosides which can be used in the present invention.

The saccharides on which the alkyloligoglycosides are based are hexoses that may be in the furanose or pyranose form. Examples of suitable hexoses include glucose, galactose, maltose, mannose and fructose. Alkyloligoglucosides are preferably used.

The alkyloligoglycosides starting material is normally sulfated as a 5 to 95% solution in a low-boiling organic solvent. The concentration of alkyloligoglycosides in solution preferably ranges from 20 to 60%.

Suitable solvents include halogenated hydrocarbons such as methylene chloride and chloroform, ethers such as diisopropyl ether and tetrahydrofuran, benzene, and carbon disulfide. Solvents having a boiling point in the range of 35° to 70° C. are preferably used. Halogenated hydrocarbons are particularly useful as a solvent. Amines, alcohols, and aldehydes, on the other hand, are unsuitable as solvents since they are not inert to sulfur trioxide and chlorosulfonic acid.

The sulfation temperature employed ranges from $-20°$ to $+100°$ C. A temperature is generally chosen that is below the boiling point of the solvent used. The temperature preferably ranges from 0° to 60° C., with room temperature being very particularly preferred. Normally, in the reaction from 0.005 to 0.5 equivalents of sulfating agent are employed per mole of OH groups in the alkyloligoglycoside.

The reaction rate is very high even under these mild conditions.

The sulfation reaction can be carried out in conventional stirred tanks. However, it is advantageous to use reactors in which the reaction occurs in a thin film. For example, gently operating falling film reactors can be used such as those described in the journal "Seifen-Ole-Fette-Wachse", No. 13, (1973), pages 360 to 365, and elsewhere. Such reactors consist essentially of a temperature controlled cylinder with a nozzle built into its head. For sulfation, a thin film of alkyloligoglycoside solution flows down on the inner wall of the cylinder, while the sulfating agent is sprayed onto the solution through the nozzle. Falling film reactors permit uniform sulfation with very short contact times.

All of the hydroxyl groups of the alkyloligoglycoside can be esterified with sulfuric acid by the process of the present invention.

The sulfation conditions are so mild that the acetal bonds are not hydrolyzed. Therefore, no long-chained alcohols or sulfuric acid esters of long-chained alcohols are obtained as by-products.

The solution remains free of particles. Conversion is practically quantitative, based on the sulfating agent which is used in less than stoichiometric amount. This makes defined sulfation possible.

With conventional sulfating agents, products are obtained that are amine-free and are therefore harmless to health. The sulfation process can be carried out continuously or discontinuously.

In the normal process of the invention, the alkyloligoglycoside is usually placed in the inert solvent first, and the sulfating agent is added. The sulfating agent can be added slowly as a liquid. On the other hand, sulfur trioxide is preferably introduced into the solution with the assistance of an inert gas, or is sprayed onto the solution through a nozzle. Sulfuric acid, chlorosulfonic acid, and the like can also be sprayed onto the reaction medium through a nozzle. After completion of the reaction, the mixture is neutralized and the solvent is removed by distillation. Salts of the sulfated alkyloligoglycosides are obtained as a residue. The free sulfuric acid half-esters of alkyloligoglycosides can be obtained from the salts by acidification.

Having now generally described this invention, a further understanding can be obtained by reference to certain specific examples which are provided herein for purposes of illustration only and are not intended to be limiting unless otherwise specified.

EXAMPLE 1

A 1.5 kg amount of a 20% solution of dodecyloligoglucoside (average degree of oligomerization of 1.5) in chloroform is placed in a 3-liter 3-necked flask equipped with a stirrer, thermometer, dropping funnel, and reflux condenser. A 203 g amount of chlorosulfonic acid (=0.5 eq/OH) is added dropwise at 20° C. over a period of 1 hour. Stirring is continued for 1 hour longer, after which the mixture is neutralized with a 10% aqueous sodium hydroxide. After distilling the solvent 1.5 kg residue of sulfated dodecyloligoglucoside is obtained. Measured acid number: 45 mg KOH/g; theoretical acid number: 55 mg KOH/g.

EXAMPLE 2

A 1.5 kg amount of a 20% solution of tetradecyloligoglucoside (average degree of oligomerization of 1.5) in methylene chloride is placed in the apparatus of Example 1. An 18 g amount of 95% sulfuric acid (=0.005 eq/OH) is then added dropwise at 0° C. over a period of 1.5 hours. The stirring is continued for 30 minutes longer, after which the mixture is neutralized with 10% aqueous potassium hydroxide. Methylene chloride is then removed by distillation. A 1.5 kg amount of sulfated tetradecyloligoglucoside is obtained as a residue. Measured acid number: 4.8 mg KOH/g; theoretical acid number: 5.5 mg KOH/g.

EXAMPLE 3

A 1.5 kg amount of a 20% solution of dodecyloligoglucoside (average degree of oligomerization of 2.5) in chloroform is placed in a 4-liter stirred pot equipped with sintered tray, stirrer, thermometer, and reflux condenser. An 86.4 g amount of sulfur trioxide (=0.3 eq/OH) diluted with nitrogen, is fed into the reaction mixture through the sintered tray from below at 20° C. over a period of 1.5 hours. The end of the reaction is determined by thin layer chromatography. The mixture is then neutralized with 10% aqueous potassium hydroxide, and the solvent is removed by distillation. A 1.5 kg amount of sulfated dodecyloligoglucoside is obtained as a residue. Measured acid number: 28 mg KOH/g; theoretical acid number: 33 mg KOH/g.

EXAMPLE 4

A 1.5 kg amount of a 20% solution of tetradecyloligoglucoside (average degree of oligomerization of 2) in chloroform is pumped through a falling film reactor (length: 1.2 m, inside diameter: 25 mm) at 20° C. At the same time, 28.4 g of sulfur trioxide diluted with nitrogen (molar ratio $SO_3/N_2 = 1:7.5$) is sprayed through a nozzle attached to the head.

The effluent solution is neutralized directly with 10% aqueous potassium hydroxide and the solvent is removed by distillation. A 1.5 kg amount of sulfated tetradecyloligoglucoside is obtained as a residue. Measured acid number: 64.9 KOH/g; theoretical acid number: 66.4 mg KOH/g

Having now fully described the invention, it will be apparent to one of ordinary skill in the art that many changes and modifications can be made thereto without departing from the spirit or scope of the invention as set forth herein.

What is claimed is:

1. A process for the sulfation of an alkyloligoglycoside having an alkyl group containing from 8 to 22 carbon atoms and having an average degree of oligomerization of 1 to 5, comprising:

Short contact time sulfating of said alkyloligoglycoside with a sulfating agent in an organic solvent having a boiling point of 30° to 100° C.

2. The process of claim 1, wherein the sulfation reaction is conducted in a solvent having a boiling point from 35° to 70° C.

3. The process of claim 1, wherein the sulfation reaction is conducted in a chlorinated hydrocarbon.

4. The process of claim 1, wherein the sulfation reaction is conducted with a 5 to 95% solution of alkyloligoglycoside.

5. The process of claim 4, wherein the sulfation reaction is conducted with a 20 to 60% solution of alkyloligoglycoside.

6. The process of claim 1, wherein said alkyloligoglycoside is an alkyloligoglycoside having an alkyl group content of 10 to 16 carbon atoms.

7. The process of claim 1, wherein the sulfation reaction is conducted at a temperature of −20° to +100° C.

8. The process of claim 7, wherein said temperature ranges from 0° to 60° C.

9. The process of claim 1, wherein the reaction is conducted in a falling film reactor.

* * * * *